United States Patent
Satoh

(12) 
(10) Patent No.: US 6,362,143 B2
(45) Date of Patent: Mar. 26, 2002

(54) DETERGENT COMPOSITIONS COMPRISING POWDERS OF RICE HULLS

(76) Inventor: Teizo Satoh, 4-12-11, Okayama-higashi, Shijonawate-shi, Osaka (JP)

( * ) Notice: Subject to any disclaimer, the term of this patent is extended or adjusted under 35 U.S.C. 154(b) by 0 days.

(21) Appl. No.: 09/847,728

(22) Filed: May 2, 2001

(30) Foreign Application Priority Data

May 29, 2000 (JP) ........................................ 2000-158272

(51) Int. Cl.$^7$ .............................................. C11D 3/382
(52) U.S. Cl. ........................ 510/130; 510/139; 510/138; 510/268; 510/368; 510/395; 510/420; 510/462
(58) Field of Search ................................. 510/139, 268, 510/395, 368, 420, 462, 130, 138

(56) References Cited

U.S. PATENT DOCUMENTS

| | | | | |
|---|---|---|---|---|
| 4,557,854 A | * | 12/1985 | Plueddemann | ......... 252/174.15 |
| 4,657,692 A | * | 4/1987 | Choy et al. | .................... 252/99 |
| 4,685,930 A | * | 8/1987 | Kasprzak | .................... 8/139.1 |

* cited by examiner

Primary Examiner—Charles Boyer
(74) Attorney, Agent, or Firm—Moonray Kojima

(57) ABSTRACT

A detergent capable of eliminating oils and fats by absorbing same thereinto, wherein a detergent comprising a surface active agent, solid detergent, liquid detergent, glycerin, or water combined with ash powders of rice hulls or carbide powders of rice hulls or a combination of the two, in a dispersed state therein. The powders become dispersed evenly on the surface of the material to be cleaned without harming the surfaces being cleaned, such as the human skin, and provides even absorption and removal of oils and fats while providing even and definite cleaning effect.

14 Claims, No Drawings

DETERGENT COMPOSITIONS COMPRISING POWDERS OF RICE HULLS

BACKGROUND OF THE INVENTION

1. Field of Invention

The present invention relates to an improved detergent which provides easier removal of oils and fats from hair, human skin or goods; and more particularly, to such detergent comprising powders of rice hulls.

2. Description of the Prior Art

Detergents used for washing items in general mainly contain a surface active agent, which agent acts to separate oils and fats from the surface of human skin or solid materials. As a surface active agent, there are, for instance, an anionic surfactant and a cationic surfactant, a nonionic surfactant and an amphoteric surfactant and so on.

On the other hand, as an absorbing material, which is porous and used to separate and recover oils from compounds of oil and water, there are known dried hulls other than porous agents of synthetic resin.

Hulls are the part-of rice (both embryo and albumen) in the hulls of ears of rice plants, also called end parts of an ear of rice plants, and are by-products produced by threshing after collection of rice. Hulls, which have been dried, have rough surfaces with surface dimension which is large and a specific gravity which is small so that the hulls have characteristics of ability to selectiely absorb oil layer floating on water surface, thus being appropriate as an absorbing agent of oil and fat. (One example thereof being Japan Patent 2,706,170)

In addition, there is disclosed in Japan Patent Publication No. Heisei 3 (1991) 77239, the use of micro powders of pulverized hulls and diatomaceous earth of approximately 0.1to 100 μm, combined to be used as a washing agent in place of the surface active agent.

Furthermore, the purpose of absorbing agents, e.g. compounds of micro powders of charcoals, other than hulls are for use as a cosmetic soap.

However, among the conventional detergents above described, those which have added the pulverized hulls onto the surface active agents, usually have particle diameters of pulverized hulls which are unevenly or evenly dispersed. Consequently, complete absorption and removal of fats and oils, were difficult.

In addition, a cosmetic soap which combines micro powders of charcoal does not have a natural feel on the skin surface because of the low hydrophilicity of the powders. This causes unnatural feeling on the skin surface. Also, it is easy to have a lump made of the soap when washing therewith.

In addition, when applying such a detergent onto the surface of a windshield of an automobile, to remove oil films, there is a problem in that uneven effects of cleaning are shown on the glass surface with the detergent being dispersed unevenly.

SUMMARY OF THE INVENTION

Thus, a purpose of the present invention is to provide a detergent capable of removing oil and fat definitely by resolving the above problems, wherein the detergent is evenly absorbed into the oils and fats attached onto the surface of human skin or items while washing same.

In addition, another purpose of the present invention is to provide a detergent capable of obtaining cleaning effect evenly and sufficiently, wherein the detergent is definitely absorbed onto the oils and fats attached onto the surface of human skin or glass or other items without harming specifically the human skin.

The present invention concerns a detergent combined with ash powders of rice hulls or carbide powders of rice hulls or compound powders using both of the same with surfactants in a dispersed state.

The detergent comprises ash powders of rice hulls or carbide powders of rice hulls or compound powders using both of the same. These powders are softer than ash powders of wood or charcoal powders that have been conventionally used. The invention comprises micro powders of the same diameter of particles and have hydrophilicity so that they are dispersed evenly on the surface of materials to be cleaned without harming the surface of the soft materials to be clean, such as human skin. Accordingly, the invention provides thorough and even absorption and removal of oils and fats.

In addition, there is provided a detergent which combines the ash powders of the rice hulls or the carbide powders of the rice hulls or using compound powders of 3 to 85 volume percent based on both of the same with solid detergent in a dispersed state.

In addition, when making a liquid detergent comprising surfactants, there is provided a detergent which combines the ash powders of the rice hulls or carbide powders of the rice hulls or using compound powders, of 3 to 85 volume percent based on both of same with liquid detergent in a dispersed state.

Furthermore, when adopting water instead of surfactant, there is provided a detergent combining the ash powder of the rice hulls or the carbide powders of the rice hulls or using compound powders of the same in 5 to 85 volume percent based on same with water in a dispersed state.

According to the invention, wherein a given amount of ash powders of rice hulls or carbide powders of rice hulls or combination thereof are combined with solid or liquid detergent, or surfactants, the powders are lubricated by the detergent or surfactants, so that the surface of the human skin or articles are not harmed even when washing same with hands using detergent thereon and oils and fats can be cleaned with water effectively.

DETAILED DESCRIPTION OF THE PREFFERED EMBODIMENTS

One example of the preferred embodiment of the present invention will be explained hereinafter. The surfactant to be used for the detergent of the present invention may be preferably selected from well known ionic surfactants, non-ionic surfactants, and amphoteric surfactants. The kinds of surfactants are not limited; however, when these are used as a skin detergent of the liquid type, they may include fluid liquid material like cream or emulsion. The surfactants are excellent in stability and are evenly dispersed without being separated, even when untouched for a length of time. Non-ionic surfactants are preferred.

For example, a non-ionic surfactant may comprise fatty acid or higher alcohol for hydrophilicity or be based on polyhydric alcohol or high molecular compound, such as hydrophilic groups, when used as a surface active agent combined for conventional cosmetic products.

The solid detergent or liquid detergent used for the invention is a detergent already prepared according to the use to be made thereof, or items to be cleaned, or a single material capable of being used as a detergent for washing with water and may be but need not include a surfactant. Furthermore, they can adopt the liquid detergent comprising a single component of glycerin.

For instance, a solid detergent is discussed below. After oils and fats comprising a suet and coconut oil are reacted with sodium hydroxide, additives, such as aromatic essence, pigments, antioxidants, or sequestering agents are added to the neat soap (melted soap with approximately 30% of water) which was salted out after adding salt thereto and become soap material of 10 to 15% water. The material is subjected to a drying step of presure reduction or hot air process. An even mixture of materials is provided to produce the soap.

Furthermore, when liquid detergent is produced, the solid soap is added as liquid components, like glycerin, to become liquid, or the melting point is lowered to shift the type of oils and fats, or by adjusting the volume of water so as to make the detergent liquid. The liquid detergent may as well be a foaming detergent comprising mainly ester alkylsulfate salt, betaine-type amphoteric surfactant, or the like.

The carbide hulls used for the invention is a material rich in carbon (amorphous carbon) after being subjected to heat dissolution wherein the hulls were heated under adequate conditions. The carbide rice hulls are produced by roasting with use of steam with a temperature of 300 to 500° C. while shutting off air.

In addition, ash powders of rice hulls used for the invention are remnants of solid ashes produced by roasting the hulls completely under good conditions.

Thus, ash powders of rice hulls or carbide powders of rice hulls or chaffs can be produced on good terms even by adjusting the volume of current air when roasting as discussed below.

The dried hulls are roasted while heaped in a mound on the earth outside. Then, the volume of current air is increase by raising the ventilating device, in the shape of a chimney, so that the device protrudes toward the top of the mound of hulls thus heaped from inside. The ventilating device may be provided with a bowl comprising porous plates, wherein the chimney, which can be in the shape of an iron cylinder is connected on the top part of the bowl, thus providing good results.

In order to produce the carbide powders of the rice hulls by using the above device, the source of fire, like a dry lumber, is first burned on the earth, above which, the bowl of the ventilating device is put on so that rice hulls are put over the bowl in a mound to keep same burning.

In this way, the surface of the rice hulls thus heaped in mound is gradually burned unevenly. The hulls are stirred by use of bars to make the whole part evenly burned black. Then, the mound is extinguished by throwing water thereon, and carbide powers of the rice hulls are thus obtained.

In addition, when the hulls are burned until they become ash white without extinguishing, ash powders of the rice hulls are obtained.

Then, the carbide powders of the hulls so obtained or the ash powders of the hulls so obtained are pulverized by a milling step, by means, for example, of an electric rotating blade for pulverization or friction so that the carbide or ash become micro particles. The size of the particles may be approximately between 1 and 50 $\mu$m or preferably 1 and 30 $\mu$m. The sizes are adopted with respect to the items to be cleaned, taking into consideration the cleaning efficiency. In order to prepare the size of the micro powders, a boring mill may be used as the pulverizing machine.

The carbide powders of rice hulls thus obtained or ash products of the rice hulls thus obtained, or the compound based on a combination of the two are dispersed after stirring and mixing evenly with the solid or liquid detergent or surfactant.

In order to stir and mix the hulls completely, a mixing machine may be used. When, liquid detergent is to be produced little by little, the pulverized solid soap and the carbide powders of the rice hulls or the ash products of the rice hulls or combination of the two, are mixed, and then heated by a strong fire inside a heat proof container. This causes melting of the soid soap and the process includes stirring and mixing the ingredients evenly by hand.

When solid detergent is to be produced, the ash powders of hulls or carbide powders of hulls or compound powders of the two combined are added to a solid detergent available on the open market, in a ratio of 3 to 85 volume percent. When the ratio is smaller than the above range, oils and fats and other dirt dirt components cannot be absorbed sufficiently. On the other hand, when the ratio is above the upper range, solid soap of the desired properties cannot be formed and solid soap thus obtained becomes so hard that it cannot be easily dissolved when washing with water.

When liquid detergent is to be produced, ash powders of rice hulls or carbide powders of rice hulls or the compound powders combining both are added to a liquid detergent available on the market,in a ratio of 3 to 50 volume percent. When, the ratio is smaller than the above range, oils and fats and other dirt components cannot be absorbed sufficiently. On the other hand, when the ratio is larger than the above range, a dispersed state of the powders in liquid detergent becomes unstable and the powders and liquid are separated even during a short term of non-use.

The detergent of the invention thus produced is capable of removing oil and fat attached onto human skin or hairs or the surface of the roots of hair or waste materials of oils and fats and the mixture of alien materials.

From the invention, a shampoo is provided which enables growth of hairs in good healthy condition. Also, a shampoo can be made from the invention which eliminates odors of dogs, cats and other pets. Moreover, the invention detergent can be used for washing and has excellent cleaning effect on collar parts where skin oils are hard to eliminate otherwise.

EXAMPLE 1

Using the above ventilating device having the shape of a chimney, the ash product was produced by heating rice hulls outside for three hours under good conditions. This product was pulverized by an electric rotating blade of a cooking mill and the powders so obtained were added to pulverized cosmetic soap (a solid) available on the market, by 40 volume percent. These were stirred and mixed after being put into a frying pan as the ingredients were heated on a gas range for 20 minutes. Then, the melted liquid compound was put into a heat proof container and cooled while being left alone. Accordingly, a solid detergent was produced in the shape of a short column.

EXAMPLE 2

A solid detergent was obtained according to Example 1, except for the following conditions. The rice hulls were heated for 2 hours outside under good conditions. When the whole part of the rice hulls turned black, carbide was found to be produced upon throwing water thereon, and roasting was stopped thereby. The product was pulverized by a cooking mill provided with an electric rotating blade.

EXAMPLE 3

A liquid detergent (cosmetic liquid soap) available on the market was added to provide 30 volume percent of the ash powders of the rice hulls which were produced in the same manner as in Example 1. The ingredients were mixed by a cooking mixer and combined in a dispersed state to produce the liquid detergent.

EXAMPLE 4

A liquid detergent (cosmetic liquid soap) available on the market, was added to provide 30 volume percent of the carbide powders of rice hulls which were produced in the same manner as in Example 1. The ingredients were mixed by a cooking mixer and combined in a dispersed state to produce the liquid detergent.

As with the detergent obtained according to Examples 1 to 4, five male and female human samplers tried using the products to wash their faces and hands. The testers found that oils disappeared definitely from the skin surface upon cleaning only once. Also, the testers found that the invention cleaned the sweat glands of the hair gland of the skin so that the skin respiration became possible, allowing thus for a fresh feeling.

EXAMPLES 5 and 6

A liquid detergent was produced, precisely, according to Example 3, except for the conditions wherein water (Example 5) or glycerin (Example 6) was used instead of liquid detergent.

EXAMPLES 7 and 8

A liquid detergent was produced, precisely, according to Example 4, except for the conditions wherein water (Example 7) or glycerin (Example 8) was used instead of the liquid detergent.

When a windshield of a vehicle was washed using the detergent of examples 5 to 8, the entire windshield was evenly washed after cleaning only once. It was confirmed that the oil film had disappeared. Also, according to Examples 7 and 8, the specified detergent, was usable for washing faces and hands and oils disappeared definitely from the surface of human skin after cleaning only once. Also, the sweat glands were readily cleaned.

EFFECTS AND ADVANTAGES OF THE INVENTION

The detergent of the invention has merit in that oils and fats attached to the surface of human skin can be absorbed evenly and be removed definitely after one washing. This results from the use of ash powders of rice hulls, or carbide powders of rice hulls, or a combination of the two, combined with surfactants, or water, or glycerin, or solid or liquid detergents, in a dispersed state.

The invention uses the surfactants, solid detergent, liquid detergent, glycerin or water, combined with the ash powders of rice hulls or carbide powders of rice hulls or a combination thereof, in a dispersed state. Such feature has merit in that the invention is capable of obtaining an outstanding cleaning effect without harming the soft surface of materials to be cleaned, other than human skin, as well as human skin.

In addition, the feature of the invention concerning the detergent, wherein a given amount of ash powders of rice hulls or carbide powders of rice hulls and others are combined in a dispersed state, adopting water instead of surfactants, has merit of providing even and definite cleaning effect and effect of removing oil films, thus providing for even absorption and removal of oil and fat.

What is claimed is:

1. A cleaning substance comprising:
   a detergent; and
   dispersed therein in a range of from 3 to 85 volume percent, an additive selected from the group consisting of a carbide powder of rice hulls, an ash powder of rice hulls, and a combination of said carbide powder of rice hulls and said ash powder of rice hulls; wherein said carbide powder is produced by roasting in steam at a suitable temperature, and wherein said ash powder is produced by roasting said hulls completely.

2. The substance of claim 1, wherein said detergent is liquid.

3. The substance of claim 1, wherein said range of additive is between 3 to 50 volume percent.

4. The substance of claim 1, wherein said additive is a combination of said carbide powder of rice hulls and said ash powder of rice hulls.

5. The substance of claim 1, wherein the particle size of said carbide powder of rice hulls and said ash powder of rice hulls is between 1 to 50 $\mu$m.

6. The substance of claim 5, wherein said particle size is between 1 to 30 $\mu$m.

7. The substance of claim 1, wherein said additive is carbide powder of rice hulls.

8. The substance of claim 1, wherein said additive is ash powder of rice hulls.

9. The substance of claim 1, wherein said detergent includes water.

10. The substance of claim 1, wherein said detergent includes glycerine.

11. The substance of claim 1, wherein said detergent is a solid.

12. The substance of claim 1, wherein said detergent comprises a surfactant.

13. The substance of claim 1, wherein said range of additives is between 5 to 85 volume percent.

14. The substance of claim 1, wherein said suitable temperature is within a range of from 300 to 500° C.

* * * * *